(12) United States Patent
Kühne et al.

(10) Patent No.: US 12,714,488 B2
(45) Date of Patent: Aug. 25, 2026

(54) ELECTROSURGICAL GENERATOR WITH MODULAR OUTPUT SOCKET FOR ELECTROSURGICAL INSTRUMENT

(71) Applicant: OLYMPUS WINTER & IBE GMBH, Hamburg (DE)

(72) Inventors: Wolfgang Kühne, Schildow (DE); Daniel Ramin, Nuthetal (DE); Benjamin Trumpold-Veselic, Teltow (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 197 days.

(21) Appl. No.: 18/373,907

(22) Filed: Sep. 27, 2023

(65) Prior Publication Data

US 2024/0108395 A1 Apr. 4, 2024

Related U.S. Application Data

(60) Provisional application No. 63/411,232, filed on Sep. 29, 2022, provisional application No. 63/411,374, filed on Sep. 29, 2022.

(51) Int. Cl.
*A61B 18/12* (2006.01)
*A61B 18/00* (2006.01)

(52) U.S. Cl.
CPC ...... *A61B 18/1233* (2013.01); *A61B 18/1206* (2013.01); *A61B 2018/00077* (2013.01); (Continued)

(58) Field of Classification Search
CPC ............ A61B 18/1233; A61B 18/1206; A61B 2018/00178
See application file for complete search history.

(56) References Cited

U.S. PATENT DOCUMENTS

2004/0097912 A1* 5/2004 Gonnering ............ H01R 27/02 606/34
2004/0133189 A1* 7/2004 Sakurai ................. A61B 34/70 606/1

(Continued)

FOREIGN PATENT DOCUMENTS

CN 113193426 A 7/2021
EP 3 758 157 A1 12/2020

(Continued)

OTHER PUBLICATIONS

Jul. 19, 2023 Search Report issued in German Patent Application No. 10 2022 125 403.8.

(Continued)

*Primary Examiner* — Sean W Collins
(74) *Attorney, Agent, or Firm* — Oliff PLC

(57) ABSTRACT

An electrosurgical generator including housing and an internal circuitry to generate a high-frequency voltage and to output the generated high-frequency voltage to an electrosurgical instrument, further including at least one output socket for connection of a plug of the electrosurgical instrument. The output socket is configured as self-contained unit including: a casing configured for mounting at a front plate of the housing; a plug socket mounted at a frontal face of the casing for plugging of the electrosurgical instrument; a conductor board inserted into the casing and being configured to provide internal connections of the output socket; and a connector provided at the conductor board for a connection to the internal circuitry. Thereby the output socket is modularly exchangeable. Being self-contained, the output socket can be easily exchanged against another output socket of different functionality, allowing for easy re-configuration.

23 Claims, 7 Drawing Sheets

(52) U.S. Cl.
CPC ............... *A61B 2018/00178* (2013.01); *A61B 2217/002* (2013.01)

(56) References Cited

U.S. PATENT DOCUMENTS

| | | | | |
|---|---|---|---|---|
| 2010/0262139 | A1 | 10/2010 | Beller et al. | |
| 2015/0229083 | A1* | 8/2015 | Bopp | H01R 13/518 439/373 |
| 2017/0312004 | A1* | 11/2017 | Allen, IV | A61B 18/1206 |
| 2019/0103699 | A1 | 4/2019 | Yamanaka | |
| 2020/0078113 | A1* | 3/2020 | Sawhney | A61B 34/20 |
| 2020/0315041 | A1 | 10/2020 | Katsumata | |
| 2020/0412668 | A1 | 12/2020 | Hiller et al. | |
| 2021/0029882 | A1 | 2/2021 | Zhao et al. | |
| 2022/0313357 | A1* | 10/2022 | Geresy | A61B 18/1206 |

FOREIGN PATENT DOCUMENTS

| | | | |
|---|---|---|---|
| JP | H04-123566 | U | 11/1992 |
| JP | 2012-64504 | A | 3/2012 |
| JP | 2014-122015 | A | 7/2014 |
| JP | 2015-150428 | A | 8/2015 |
| JP | 2017-524483 | A | 8/2017 |
| JP | 2019-67602 | A | 4/2019 |
| JP | 2020-161373 | A | 10/2020 |

OTHER PUBLICATIONS

Jul. 27, 2023 Search Report issued in German Patent Application No. 10 2022 125 312.0.

* cited by examiner 3
5
3'
5'
5'
11
5"
3"
14

18
8
3'
11
3'
3
3"
14

3'
8
18
3
7
31

4
45
5
51
3
74
7
4

71
70
72
6
75

81I
42
49
41
4

43
44II
4
47
41
11

4
44
43
41
5
44

47
4
46
41
5
44

4
80
44
41
5
44

81
11
80
47'
4
5
41
80
44
11
81

4
5
80
44
41

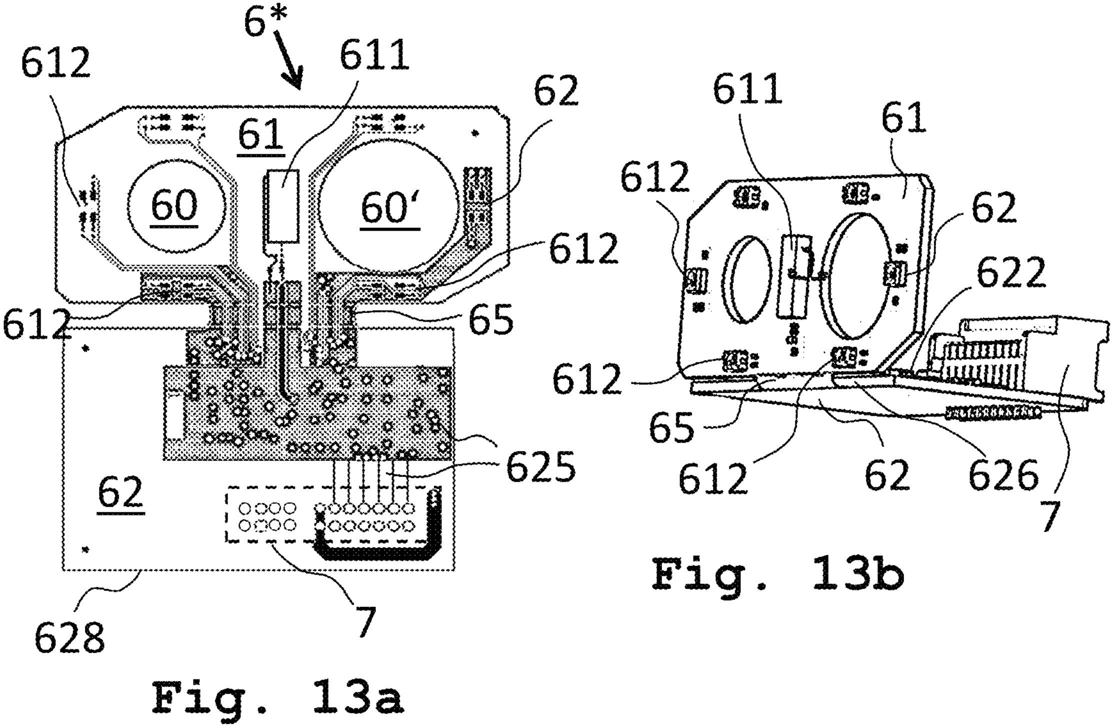
Fig. 13a
Fig. 13b
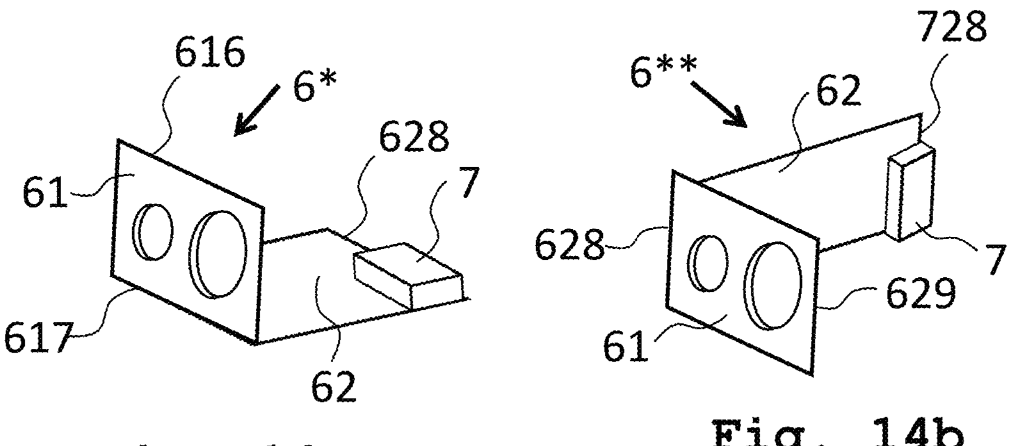
Fig. 14a
Fig. 14b

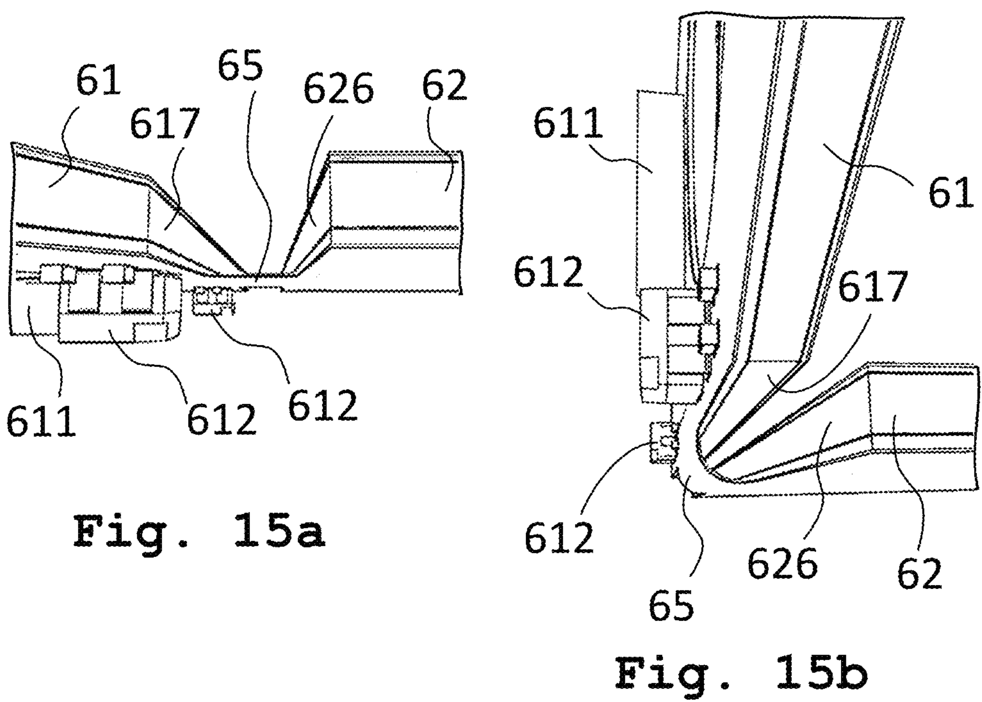
Fig. 15a
Fig. 15b
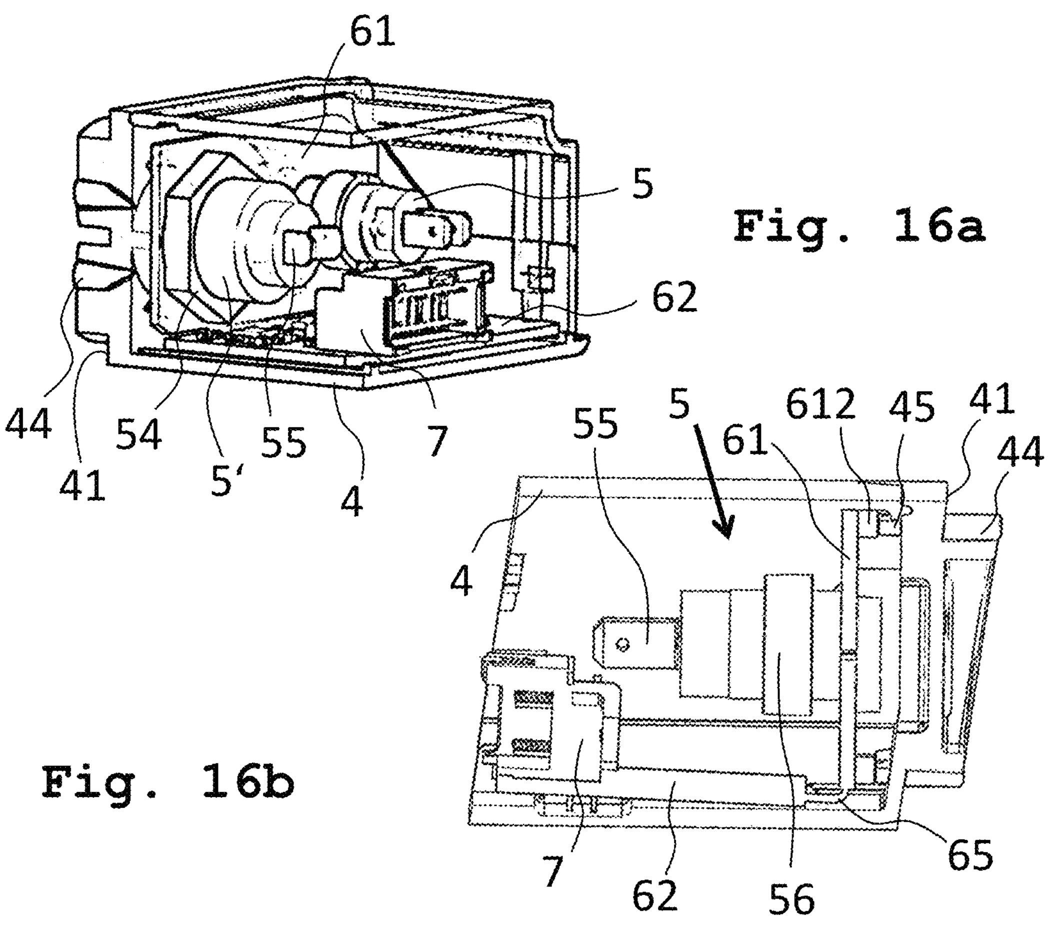
Fig. 16a
Fig. 16b

ELECTROSURGICAL GENERATOR WITH MODULAR OUTPUT SOCKET FOR ELECTROSURGICAL INSTRUMENT

The invention concerns an electrosurgical generator. The electrosurgical generator comprises an internal circuitry designed to generate a high-frequency voltage and to output the generated high-frequency voltage to an electrosurgical instrument. It comprises at least one output socket for connection of a plug of the electrosurgical instrument.

Electrosurgical generators find widespread use in surgery. They are used for a variety of tasks in different fields of surgery, and various kinds and types of instruments are connected to the electrosurgical generator, said instruments being designed and configured specially for the surgical task to be accomplished. For this reason, depending on the functionality desired, different kinds of electrosurgical instruments are provided that require different output sockets. For example, there are monopolar and bipolar instruments requiring monopolar and bipolar output sockets. Moreover, there are also universal output sockets being specially configured as to accept monopolar as well as bipolar electrosurgical instruments. Conventionally, these output sockets are individually mounted to a front plate of the electrosurgical generator and wired individually in single conductor technology. This provides for a rather laborious assembly which is, due to the traditional single-conductor wiring, also prone to errors in performing the wiring. This is even more relevant for modern electrosurgical generators which tend to have more than one output socket, e.g. three or more.

It is known to provide electrosurgical generators with output sockets having visibly different shapes depending on the type of output socket, thereby providing a visual cue to the user about the type of the output socket (e.g.: Olympus ESG-410 generators). From a user perspective, this is beneficial in terms of reducing errors in plugging-in of different instruments. However, this does nothing for reducing the laborious and complex assembling task for the manufacturer which is also error-prone. This drawback gets worse with a higher number of different output sockets.

An electrosurgical generator is known that is equipped with modular units for output sockets which are exchangeable in the field (EP 3 758 157 A1). Said modular unit for an output socket may be exchanged against a service module which is provided at its rear side with a mechanical cover of the HF supply and further allows access to an internal service interface (USB-Port), thereby increasing operational safety for servicing.

Accordingly, there is a need for improved electrosurgical generators being easier to assemble and to wire for different output sockets.

The solution according to the invention is found in the features of the independent claim. Advantageous developments are the subject matter of the dependent claims.

In an electrosurgical generator comprising a housing and an internal circuitry designed to generate a high-frequency voltage and to output the generated high-frequency voltage to an electrosurgical instrument, further comprising at least one output socket for connection of a plug of an electrosurgical instrument, said at least one output socket is configured as a self-contained unit comprising a casing configured for mounting at a front plate of the housing, and a plug socket mounted at a frontal face of the casing for plugging of the electrosurgical instrument; according to the invention the at least one output socket is further provided with a conductor board being inserted into the casing and being configured to provide internal connections of the output socket; and a connector provided at the conductor board for a connection to the internal circuitry of the electrosurgical generator.

A few terms should first be explained below:

In the field of electrosurgical generators, "high frequency" refers to frequencies typically in the range between 100 kHz and 4000 kHz.

"High voltage" typically refers to voltages up to 10 kV, preferably up to 4000 V.

The core of the invention is to provide an output socket that is self-contained, in particular features its own casing carrying the actual plug socket and conductor board. It is modularly exchangeable. Accordingly, the output socket can be easily exchanged against another output socket having a different functionality. Thereby, the electrosurgical generator can be easily adapted to a different functionality by inserting a different output socket to the front of the housing. This allows for an increased efficiency in manufacturing a range of different electrosurgical generators having a variety of different output sockets. By the connector being a part of the output socket, it is always ensured that the required connections are to be made without the risk of confusion or incomplete connection as it is inherent with a plurality of single conductor connections according to the prior art. The invention thus provides a self-contained output socket having defined mechanical and electrical/functional boundaries. This increases exchangeability between output socket having different functionality while maintaining ease of manufacture, requiring less adaption of the front plate of the electrosurgical generator to which the output sockets are to be mounted, and further minimizes the risk of incomplete or wrongly made electrical connections from the output socket to the internal circuitry of the electrosurgical generator.

These advantages can be further increased by the at least one output socket being selected from a group of output sockets being configured differently, in particular configured differently for accepting different electrosurgical instruments, and the casings of the output sockets of said group having an identically sized and contoured external perimeter. Accordingly, the different output sockets have casings featuring the same external perimeter, thereby allowing the casings of the various output sockets to be placed into identically shaped cutouts of the frontal plate of the electrosurgical generator. By virtue of this, owing to such uniform casing no mechanical adaptions are necessary to mount different output sockets. The term "contoured" is understood to relate to the external contour, in particular along a perimeter defined by bottom, top and both lateral sides of the casing as it is to be used for placing the casing in a cutout.

It is beneficial if the connector is mounted directly on the conductor board. However, this is not a necessity as an indirect mounting, e.g. via a multi-stranded cable, may suffice.

Preferably, the conductor board is selected from a plurality of conductor boards having different functionality, said conductor boards being mechanically exchangeable in the casing. Thereby, a different conductor board having a different functionality can be inserted into the casing without any additional mechanical alterations, thereby enabling a modular exchange of the conductor boards.

Advantageously, the conductor board is provided with a control electronic component, in particular (but not limited to) for light emitting devices and/or contactless interface. Said control electronic component may in particular be a microprocessor. By virtue of the microprocessor, the output socket gains processing facility on its own. Thus the output socket is no longer totally dependent on the main control unit, but rather is provided with its own "intelligence". It is thus enabled to become an active part like a smart device. The output socket can e.g. independently check and verify whether it may properly be used in said specific electrosurgical generator, or whether it was illegitimately put in and thus will block itself for the sake of surgical safety; likewise it can perform corresponding checks on the actual electrosurgical instrument plugged into said output socket. Further, the output socket is thus enabled to provide signaling, be it to the main control unit, to the electrosurgical instrument or to the user (e.g. by lighting signals), as will be detailed later.

Preferably, the control electronic component is communicatively connected to a control unit of the internal circuitry, wherein preferably the control electronic component is configured to perform instrument related data processing as a sub-station to the control unit, and/or to control the electrosurgical instrument by means of a prescribed process, said prescribed process comprising a sequence of activation steps for the electrosurgical instrument. By such a process, activation time and characteristics for electrosurgical instrument can be implemented locally at the output socket, and/or they are being conveyed to the output socket and its control electronic component from the internal circuitry. Such an active interaction with the main control of the electrosurgical generator at one side and/or with the electrosurgical instrument at the other side is particularly useful for complex surgical procedures of the electrosurgical generator and the electrosurgical instrument attached thereto. This is further particularly useful for complex modes of operation requiring close interaction of the electrosurgical generator and the electrosurgical instrument, thereby enhancing surgical effectiveness as well as patient safety.

Preferably, the conductor board is further provided with a signaling device, preferably a light-emitting device like a LED, interacting with the control electronic component for signaling status information to a user, preferably status information of the internal circuitry, the electrosurgical instrument, and/or the prescribed process. Thereby, in particular in combination with an actively driven lighting provided at the output socket, a useful communication link to the user can be established which aids the user in performing the right steps of the surgical procedure at the right time, e.g. as prescribed by said process. This is another valuable contribution to surgical effectiveness as well as patient safety.

Advantageously, the conductor board is provided with a module identifying unit configured to communicate with the internal circuitry, the module identifying unit being further configured to identify type and/or functionality of the output socket. Thereby the actual conductor board inserted into the output socket can identify itself and therefore provide the internal circuitry of the electrosurgical generator, in particular its control unit, with information about the output sockets and their respective functionality as they are actually mounted in that electrosurgical generator. This allows for an integrity check of the electrosurgical generator and its output sockets, thereby increasing safety against mismatched output sockets. Thereby it can be ensured that the electrosurgical generator only interacts with the output sockets and electrosurgical instruments for which said electrosurgical generator was designed, configured and has been officially approved.

Preferably, the conductor board is provided with a contactless interface configured to communicate with the electrosurgical instrument, in particular its plug. Thereby, a communicating functionality with the electrosurgical instrument can be achieved by the conductor board. The interface can be configured to be operated in various different kinds. For example, the interface may comprise a proximity sensor configured to detect presence of the plug to be plugged-in to the output socket, thereby it can be established whether an electrosurgical instrument is actually plugged into the output socket or not. It thus can serve as a kind of presence detector and report the status of being plugged-in to the internal circuitry of the electrosurgical generator via the connector. Further, the contactless interface may be configured as a data interface to the plug, thereby enabling communication with the electrosurgical instrument. This can be realized e.g. by RFID. Thereby data stored on the electrosurgical instrument can be read out to the electrosurgical generator, like specific modes or parameters to be employed for usage of said specific electrosurgical instrument, and/or data can be written to the electrosurgical instrument, like usage time of number of usage cycles.

Preferably, a supplementary data interface is provided on the conductor board and is configured to communicate with signaling devices on the electrosurgical instruments, in particular a hand switch and/or a data source of the electrosurgical instrument. The supplementary data interfaces may be contactless or may have contacts. By virtue of this, signals created at a certain electrosurgical instrument, like activation of a hand switch, can be communicated to the conductor board. Further, thereby another option is provided to read out a data source of the electrosurgical instrument.

Advantageously, the conductor board can also be provided with driving electronic components for light-emitting devices and/or contactless interface, said contactless interface being configured to communicate with the electrosurgical instrument, in particular its plug, preferably comprising a proximity sensor configured to detect presence of the plug to be plugged-in to the output socket, and/or a data interface to the plug. Thereby, concerning driving or controlling functionalities of the conductor board, the output socket with its conductor board becomes independent of the internal circuitry of the electrosurgical generator. This further enhances the self-contained philosophy of the output socket according to the present invention. By having its own driving and/or controlling components, the conductor board and the output socket not only become independent from the electrosurgical generator, but it is also ensured that always the correct driving/control components for their respective output socket are provided on the conductor board. This reduces the risk of any mismatch between driver component and driven functionality as it could be encountered if the driver component were present centrally in the internal circuitry of the electrosurgical generator. Accordingly, ease of assembly as well as operational safety are increased.

In order to achieve the aforementioned communication and interoperability of the local control electronic component (microprocessor) of the output socket, the control electronic component is configured to interact with at least one of the group comprising module identifying unit, supplementary data interface, driving components for light emitting devices and contactless interface.

In an advantageous embodiment, the casing is provided with a light guide configured for illuminating a front portion of the casing. Thereby, the casing does not only provide mechanical support and protection for the output socket and its conductor board as well as plug socket, but also actively participates in functionality. By virtue of the light guide in a front portion of the casing the actual plug socket into which the electrosurgical instrument is to be plugged in can be illuminated, thereby facilitating usage.

Advantageously, the light guide is provided with an extension being configured for a remote light feed, preferably a light-emitting device forming a part of the internal circuitry. The term "remote" is to be understood such as to refer to a light feed which is external to the output socket, i.e. is not part of the output socket. Typically, said remote light feed will be within the housing of the electrosurgical generator, preferably it is a part of its internal circuitry.

Preferably, the casing is provided with a receptacle for a light-emitting device, preferably a LED, and/or the conductor board is provided with a light-emitting device, in particular LED. Thereby, the lighting can be achieved passively in particular by employing a light guide with a remote located light-emitting device, e.g. LED mounted at a fixed location within the housing of the electrosurgical generator. Alternatively or additionally, the lighting can be achieved actively by providing a light-emitting device, in particular an LED, at the output socket, preferably at the conductor board thereof. This further increases the self-sufficiency of the output socket.

Further preferably, the light-emitting device is configured for supplying light into the light guide, preferably it is covered by the light guide, and/or into a translucent insert which is preferably colored. This enables the light from the light-emitting device, particularly a LED, to be conveyed via light guide. Alternatively, the light emitted from the LED can be can be radiated directly to the frontal face and therefore into the field of vision of the user. A translucent element may be used for protection of the light-emitting device, as well as for achieving an effective and inexpensive coloring of the radiated light.

Advantageously, the casing is provided with a surrounding frame carrying at least one light-emitting device, said frame being configured for attachment to the frontal plate of the casing. Thereby, the light-emitting device and the board on which it is attached can doubly serve also as a frame for a proper mounting the output socket. Thereby a higher degree of integration can be achieved. Further, this facilitates manufacturing. The light-emitting device may radiate its light directly towards the user. However, preferably, a translucent front cover is provided for the frame with its at least one light-emitting device, said translucent front cover and/or the frame being provided with a sealing configured to interact with the frontal plate. This provides for more diffuse lighting as well as highlighting the contour of the output socket to the user. The sealing shields against influx of unwanted matter and/or reduces leakage of HF radiation, as further explained subsequently with respect to HF-sealing.

Further preferably, said translucent front cover may be configured for indirect lighting by having the at least one light-emitting device offset such as to be at least partly covered by the frontal plate. This avoids direct radiation of light into the user's eye and therefore achieves with minimal effort an indirect lighting which has a benefit as being less straining for the eyes of the surgeon.

The conductor board which is an integral part of the output socket provides the necessary lighting by means of a light-emitting device, preferably a LED, thereby ensuring supply of the necessary lighting at the place where it is needed. Due to the defined relationship between the conductor board and the casing, it is preferable to have the light-emitting device placed at a defined position such that it is located in front of an entry to the light guide. Thereby, the light-emitting device is correctly positioned upon inserting the conductor board into the casing. Further, on the various different conductor boards the light-emitting device is preferably placed at a unitary position. Thereby, it can be achieved that the light-emitting device is placed in the correct position at the light guide regardless of the actual conductor board being utilized.

Further, it is preferred that the light-emitting device is configured for emitting light of different colors. Thereby it is achieved that the light provided by the light guide not only serves the purpose of illumination but also can be used for optical signaling, like communicating ready states ("green light"), caution warnings ("orange light") and/or danger or fault states ("red light").

Advantageously, at least one cutout is provided at an edge of the casing, said cutout having an opening to a frontal face of the casing and being configured as receptacle for a light guide or a light emitting device, preferably a series of cutouts is provided. Such cutouts can be efficiently manufactured and therefore receptacles for lighting elements, be it passive or active, as well as proper positioning of the lighting elements can be achieved. The cutouts are preferably integrated into the casing of the output socket, thereby leaving the external surfaces of the socket's casing untouched, thus avoiding any sealing difficulties which may otherwise occur.

Preferably, a seating for an illumination board is provided at the cutout, the illumination board carrying at least one light-emitting device, preferably at least one LED, further preferably a plurality of LEDs being spaced to match a spacing of the series of cutouts. Thereby, an active lighting at the correct positions as determined by the cutouts can be achieved with a minimum effort.

Additionally or alternatively to the LED lighting, a light guide can be positioned within the cutout or series of cutouts such as to emit light therethrough to the frontal face. This provides for passive lighting, enabling use of a remote light source, e.g. fixed within the housing of the electrosurgical generator, and therefore obviates the need for an own lighting element at the output socket. This allows for free positioning of the remote light source, thereby giving a further degree of freedom. Preferably, the cutouts of the series are in line with each other, preferably enabling a single light guide to be threaded through them. Thereby, proper manufacturing as well as ease of proper positioning can be achieved with minimum effort.

Advantageously, the frontal face of the casing, at least in a region of the plug socket, is formed by a planar light guide, preferably being provided with a masking having a masking hole around the plug socket. This allows for direct illumination of the immediate surrounding, e.g. ring-shaped, of the plug socket and therefore facilitates insertion of the plug of the electrosurgical instrument. This aides the user in finding the correct spot for inserting the plug.

Preferably, the planar light guide is oriented perpendicular to a plugging direction of the plug socket, and light is provided by a light-emitting device positioned at an edge of the planar light guide and/or by a second light guide connecting to said planar light guide. Such an arrangement is easy to manufacture and to assemble and further provides for a compact arrangement of the light-emitting device as well as of the planar light guide.

Advantageously, the plug socket comprises a hollow interior and an opening is provided at a rear end of the plug socket, wherein a light-emitting device is positioned at said opening and being configured to emit light through the hollow interior to the frontal face of the casing. This allows placing of the light-emitting device, in particular an LED, at the open rear end of the actual plug socket, thereby projecting the light through the interior hole of the plug socket towards the user. This provides a perfect orientation aid for guiding the plug into the intended plug socket. To this end, the plug socket is preferably provided with a sleeve as an internal contact for the plug of the electrosurgical instrument, and optionally a translucent element is positioned within said sleeve. The translucent element provides for additional protection against any risk of direct contacting of the sleeve and a high-voltage, and additionally allows for coloring of the light emitted.

Advantageously, the casing is provided with a circumferential HF sealing, preferably configured such as to bear on the frontal plate in its mounted state. Thereby, the casing is equipped with its own sealing and therefore can be affixed in a HF-tight manner to the frontal plate of the electrosurgical generator automatically by mounting the output socket. Thereby, any need for additional sealing is avoided, thus further increasing ease of assembly as well as operational safety.

It may be beneficial, in particular for creation of more complex types of electrosurgical generators, to provide a second group of casings having a different external perimeter. This allows to make a distinction, in particular with respect to such output sockets being configured for different kinds of electrosurgical instruments, like ultrasound instruments or advanced instruments having a combination of bipolar high-frequency and ultrasound functionality (e.g. like "Thunder-beat" instruments of Olympus Surgery).

Preferably, the at least one output socket comprises an integrated high-frequency conductor line. By virtue of this, also the distribution of the high-frequency voltage as generated by the inverter of the electrosurgical generator can be achieved at the output socket, thereby obviating the traditional need for a separate connection from the inverter to the output socket. This further facilitates assembling and increases modularity. This can be further enhanced by having the high-frequency conductor line being comprised in the connector, preferably with a separator or in a dedicated sub-connector for protection of the signal lines, and terminating at the plug socket. Thereby, the conductor line for the high-frequency voltage can be placed in the same conductor as other supply and signal lines to and from the output socket. By virtue of such a separator a sufficient isolation of the high-voltage is achieved. The separator may be a structural element but may also be a spatial separation by a predefined minimum distance (as appropriate for the relevant high voltage in the kilovolt range). Having high-voltage and other lines combined in one connector further facilitates assembly and reduces any risk of incomplete or wrongly made wiring.

In a particularly preferred embodiment of the electrosurgical generator that may even deserve independent protection, the at least one output socket comprises a casing for affixing a printed circuit board at a predefined position and a front face for the plug socket, wherein said printed circuit board is configured as an angled printed circuit board assembly comprising a vertically extending conductor board located adjacent to a front of the casing, a horizontally extending conductor board being located rearward of the vertically extending conductor board and being oriented such as to point rearward, and an inter-connector providing electrical connections between said conductor boards, the horizontally extending conductor board is provided with a connector for connection to the internal circuitry and with conductors for conveying electrical energy to the vertically extending conductor board.

Accordingly, the conductor board is preferably being configured as an angled assembly. The horizontally extending board utilizes space just below and particularly behind and around the plug socket, thereby making use of dead space behind the plug socket which was hitherto largely unused apart from the high-frequency cable supplying the plug socket. The horizontally and vertically extending conductor boards can be connected prior to insertion, thereby facilitating assembly. Further, the horizontally extending conductor board comprises conductors that deliver electrical power to the vertically extending board, thereby accomplishing power supply of the vertically extending board without requiring additional assembly steps. Therefore, a beneficial combination is realized of a space-saving concept and a concept that facilitates assembly.

Moreover, further components that may be required for additional functionality can be placed on the horizontally extending board. Owing to the orientation of this board to be extending in the horizontal direction it does not require any additional frontal area, so enhances the space saving.

Further, in addition to the space saving, the angled configuration provides unhindered access to the plug socket, such that it allows for a direct routing of the high-frequency high voltage to the plug socket, in particular to a back side of the plug socket where its contacts are usually located. Consequently, assembling of the power connection is further facilitated.

Yet further, due to the angled configuration any high-frequency high-power routed via the horizontally extending conductor board to the plug socket can be kept away from the vertically extending board and any sensors, in particular proximity sensors, which may be placed on the vertically extending board. In addition, this allows for a rather short distance to be travelled by the high-frequency high voltage and therefore minimizes electromagnetic emission. This results in a minimization of unwanted interference that may adversely affect sensors placed on the vertically extending board.

As a result, the preferred angled arrangement combines benefits in electrical configuration, in particular minimizing HF emission, with ease of manufacturing due to lessened space requirements and improved access.

Preferably, the vertically extending conductor board is provided with at least one light source configured to emitting light for illuminating the plug socket. By placing the light source on the vertically extending conductor board optical transmission losses for illumination of the output socket and its plug socket are minimized, and the electric power required for supply of the light can be conveyed by means of the conductors of the horizontally extending board via the interconnector without requiring additional assembly work.

Advantageously, said light guide comprises a light entry portion, in front of which the light source mounted on the vertically extended conductor board is positioned. Due to the light entry portion at this location, it can be ensured that in an assembled state when the vertically extending conductor board is put in its place then automatically the light source is located such as to be in a correct position relative to the light entry, so that the light emitted from the light source can directly and effectively enter the light guide.

Advantageously, the vertically extending conductor board is further provided with a sensor configured to detect if the plug is positioned in the plug socket. By having the sensor placed on that board, the sensor will be automatically in a position close to the plug to be detected without requiring any additional mounting or laborious manual position adjustments of the sensor. Thereby a more reliable detection as well as lesser effort on assembly can be achieved. In a preferred embodiment, the sensor is a proximity sensor, in particular of a RFID type. A proximity sensor allows for contactless detection which provides more freedom in positioning than a sensor of a physical contact type, and further avoids sensor degradation due to wear as it would be inevitably encountered with a sensor of the physical contact type.

Preferably, the inter-connector between the conductor boards is a flexible inter-connector. This allows for easier positioning and assembly since angular variation or other minor positional deviations could be more easily tolerated by such a flexible inter-connector. In an advantageous embodiment, the flexible inter-connector is attached in a fixed, in particular plugless, manner at one or both of said conductor boards. Thereby the number of joint connections can be reduced which is beneficial for reliability and longevity for safeguarding electrical continuity.

In a particularly advantageous embodiment, that may warrant independent protection, the horizontally extending conductor board, the flexible inter-connector and the vertically extending conductor board are formed as a unitary piece, preferably by a rigid-flex printed circuit board (PCB). Such rigid-flex printed circuit board offer the possibility of a secure connection with the additional benefit of contact reliability as well as a reduction in plug and connector components. The flexible inter-connector being affixed to the conductor boards guarantees that polarity reversal or wrong inter-board connections cannot happen. Even complex connections can be made in a reliable and robust manner. Said rigid-flex printed circuit board may have its flexible inter-connector arranged symmetrically with inwardly located flexible layer (usually at the middle of a thickness of the PCB) or asymmetrically with outwardly located flexible layer, the latter being preferred for usage at the confined space of the output socket.

Advantageously, conductors of the conductor boards are configured as impedance-controlled conductors, preferably conductors of the inter-connector are also configured as being impedance-controlled. Such impedance-controlled conductors allow for a precise control of apparent impedance and characteristic wave impedance. Thereby even fast signals and high-frequency voltages can be conveyed with a minimum of losses and a minimum of reflections. Such impedance-controlled conductors not only feature rather low values for losses and reflection, but they also have the benefit that the impedance is rather constant along the line. This ensures signal stability and further reduces electromagnetic emissions, which is a valuable advantage in the context of electrosurgical generators used in a sensitive environment.

It is beneficial if the connector is mounted directly on the horizontally extending conductor board, preferably along its rear edge. Assembly is facilitated by not having to deal with a movable connector. However, this is not a must as there may be cases where an indirect mounting of the connector to the horizontally extending conductor board suffices, e.g. by a multi-stranded cable.

Preferably, a high-frequency line supplying the high-frequency voltage to the output socket comprises a direct connection from the connector to the plug socket, said direct connection bypassing the inter-connector between the conductor boards. This is particularly useful for conveying the high-power high-frequency voltage signal directly to the plug sockets, thereby unloading the inter-connector between the conductor boards from the associated high-voltages and high power. Further, by such a direct connection a shorter wiring can be used, thereby contributing to reducing electromagnetic emissions.

In an advantageous embodiment, the vertically extending board is provided with a clearance hole for the plug socket, the clearance hole being configured for allowing passage of a body of the plug socket. By virtue of such clearance hole, the plug socket can with its body reach through the vertically extending conductor board, thereby allowing contacting from behind and allowing fixation of the plug socket at the front face. The front face plate is preferably a plate affixed to the casing, advantageously said front face plate and the casing are formed as a unitary piece. Thereby, a structurally beneficial and solid fixing of the plug socket can be achieved with the additional benefit that the angled printed circuit board assembly, in particular the vertically extending conductor board, is kept free of mechanical loads induced by said fixing. Thereby the considerable load that may be induced by repetitive plugging and unplugging of electrosurgical instruments to the plug socket does not have detrimental effect on the angled printed circuit board assembly and its electrical connections. This increases robustness of the output socket.—However, it shall not be ruled out that the plug socket may be affixed at the vertically extending conductor board.

Advantageously, a clamping device may be provided that is configured to affix the vertically extending conductor board at the plug socket. Herewith a mechanical connection between the plug socket and the vertically extending conductor board is achieved, which helps stabilizing the position of said conductor board and protecting it from dislocation, e.g. if the electrosurgical generator is transported.

Concerning the relative arrangement of the horizontally and vertically extending conductor boards, in most cases the horizontally extending conductor board is positioned adjacent to a lower or upper edge of the vertically extending conductor board. This has a benefit of providing sufficient space for placing additional components on the horizontally extending conductor board, e.g. for providing additional advanced functionality. However, it may also be possible to position the horizontally extending conductor board along the left or right lateral edge of the vertically extending conductor board. This has the benefit of creating a large free center space behind the plug socket. This improves accessibility to the plug socket itself and further helps in removing heat. In particular if the electrosurgical generator is a rather complex one having several output sockets stacked on top of each other, the free center space allows for an unrestricted upward rising of warm air and thereby removal of heat.

The invention is explained in more detail below with reference to an advantageous exemplary embodiment. In the figures.

Figures 3A, 3B, 4A, 4B:
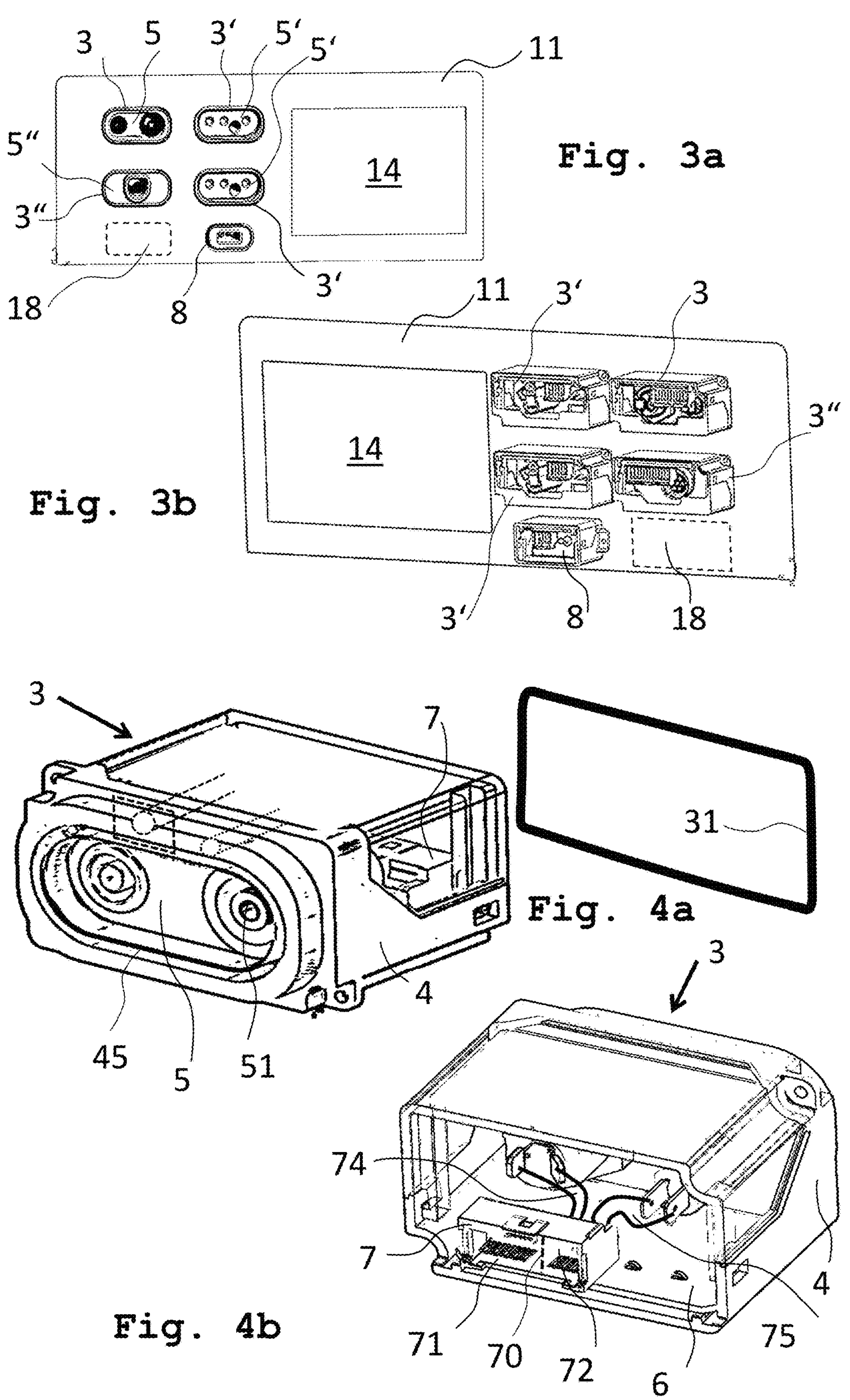
Figures 5, 6A, 6B:
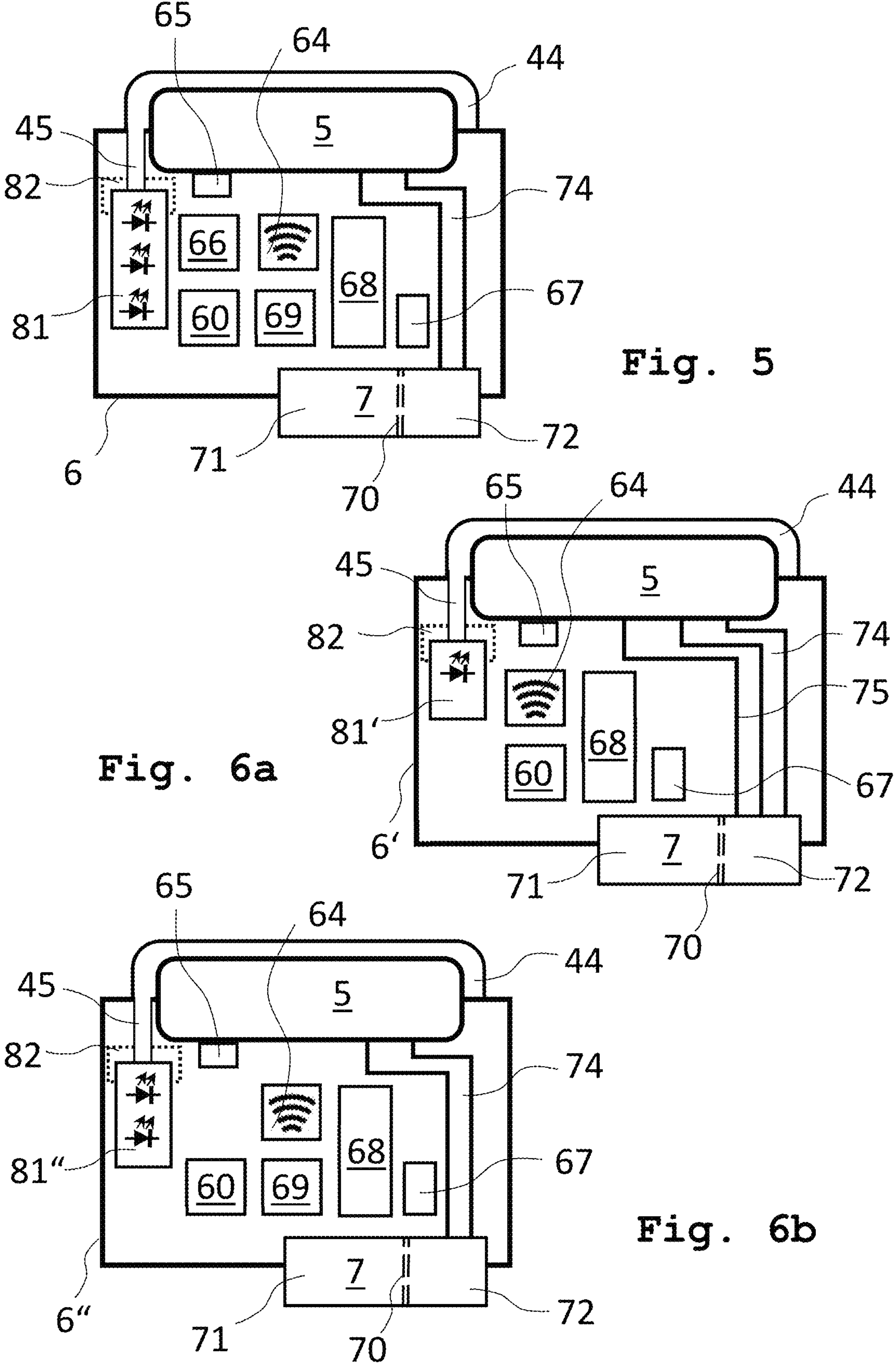
Figures 7, 8A, 8B, 8C, 9A, 9B, 9C:
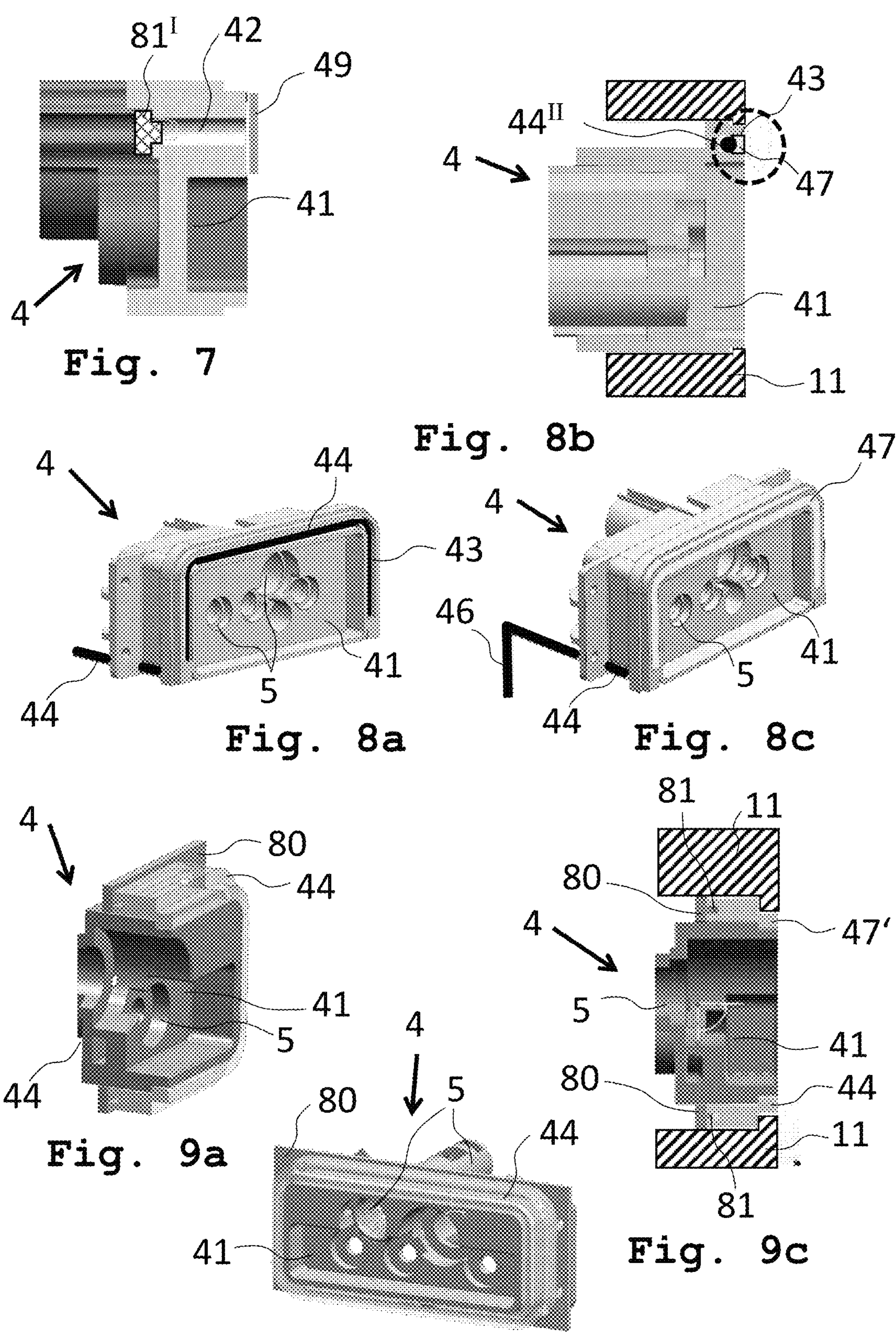
Figures 10A, 10B, 11A, 11B, 12A, 12B:
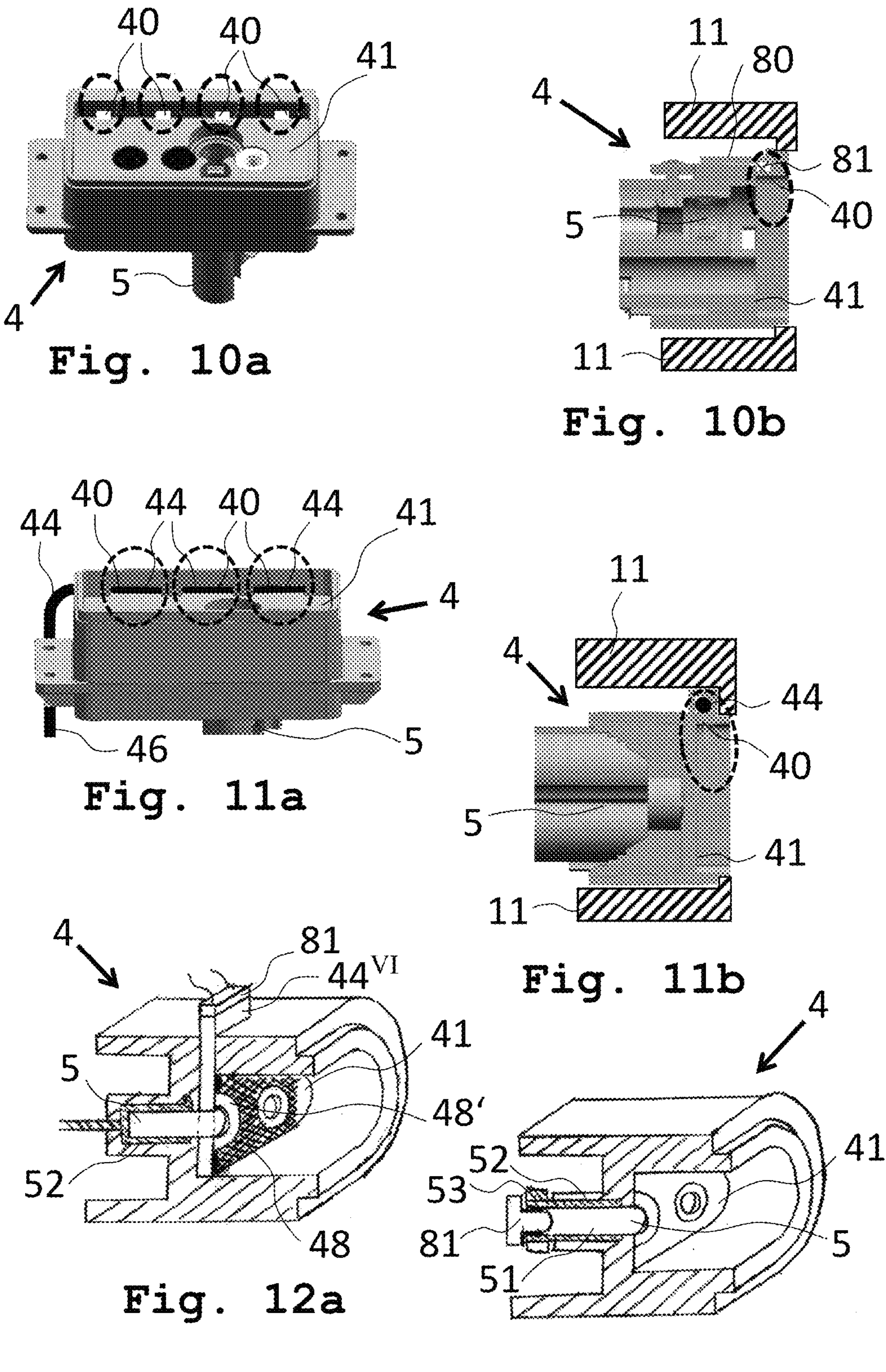

FIG. 3*a, b* show a frontal and rear view, respectively, of a front plate of a housing of the electrosurgical generator;

FIG. 4*a, b* show a perspective frontal and rear view of a casing of an output socket of the electrosurgical generator;

FIG. 5 shows a schematic view of a conductor board of the output socket;

FIG. 6*a, b* show alternative embodiments of the conductor board which are modularly exchangeable;

FIG. 7 shows a first variant of providing lighting at a frontal face of the casing by LED;

FIG. 8*a-c* show a second variant of providing lighting by light guide;

FIG. 9*a-c* show a third variant of providing lighting by a LED board as a frame;

FIG. 10*a, b* show a fourth variant of providing lighting indirectly by LED;

FIG. 11*a, b* show a fifth variant of providing lighting indirectly by light guide;

FIG. 12*a, b* show a sixth and seventh variant of providing lighting by light guide;

FIG. 13*a, b* show a bottom view of circuit board assembly in a flat state and a perspective view of the circuit board assembly in an angled state;

FIG. 14*a, b* show schematic views of alternate configurations of an angled circuit board assembly;

FIG. 15*a, b* show detail views of an inter-connector of the circuit board assembly in a flat and angled state; and FIG. 16*a, b* show a perspective view and a cross-section of the assembled output socket in a ready-to-mount state.

Figure 1:
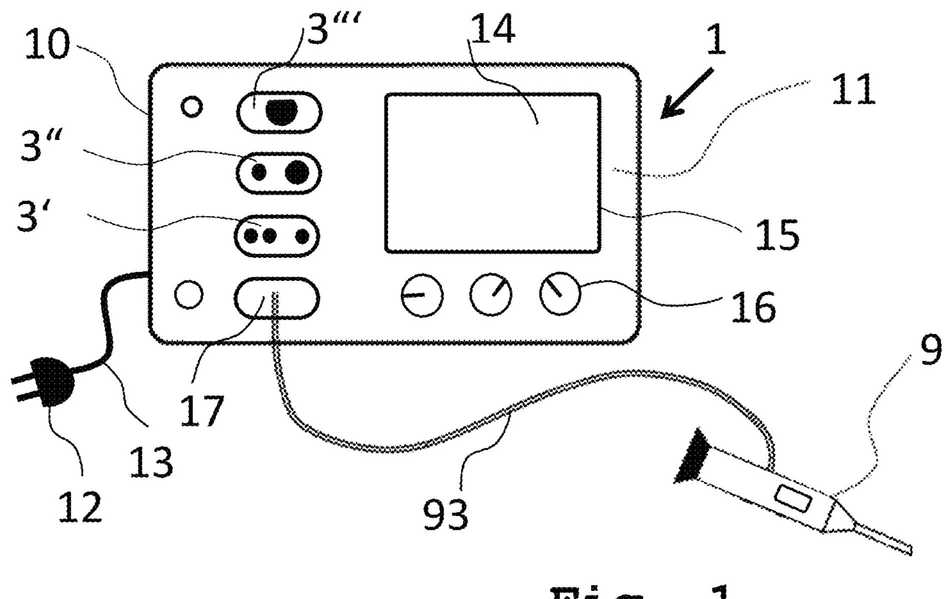
FIG. 1 shows an electrosurgical generator according to an exemplary embodiment with an attached electrosurgical instrument.

An electrosurgical generator according to an exemplary embodiment of the invention is illustrated in FIG. 1. The electrosurgical generator, identified as a whole by reference numeral 1, comprises a housing 10 having at least one output socket 3 (in the depicted exemplary embodiment a total of four output sockets 3', 3', 3") for connection of an electrosurgical instrument 9. A power supply cable 13 with a mains plug 12 is provided which is connectable to an electrical power source which may be an electricity grid, like AC mains in a building, or an off-grid source of electric energy, like a 12 Volt or 24 Volt battery in a vehicle or mobile hospital. Further, a user interface 14 is provided comprising a display 15 and an input device like knobs 16 for inputs by the user. The display 15 shows information concerning the inputs made by the user and the status of the electrosurgical generator 1. By virtue of the user interface 14 the user can issue directions and commands to a control unit 20 which controls operation of the electrosurgical generator 1 and its components, including frequency and voltage of the AC voltage emitted by the output socket 3 as well as modes of operation.

Figure 2:
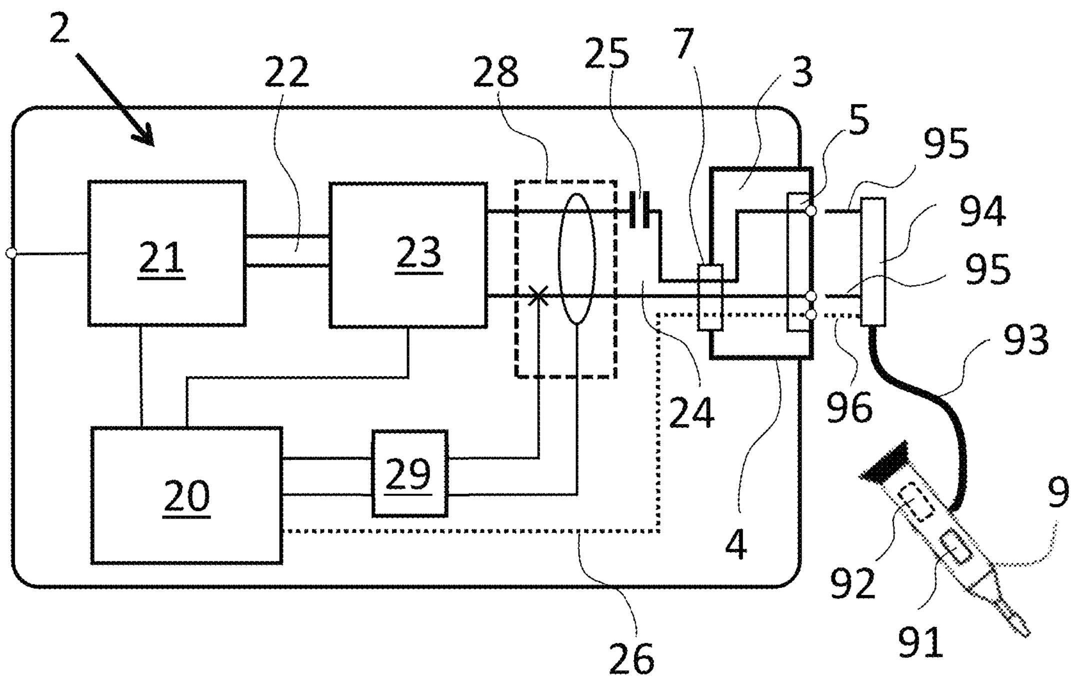
FIG. 2 shows a schematic functional diagram of the electrosurgical generator according to FIG. 1.

Said electrosurgical instrument comprises a cable 93 with a high voltage plug 94 which is to be plugged-in into the output socket 3 in order to supply the high-frequency alternating voltage for operation of the electrosurgical instrument 9. FIG. 2 shows a schematic functional diagram of an internal circuitry 2 of the electrosurgical generator 1. It comprises a power supply unit 21 that is fed with electrical energy by the supply cable 13, the power supply unit 21 feeding a DC bus 22 connected to an inverter 23 configured for generating high-frequency alternating current in a high-voltage range of a few kilovolts. Operation of the inverter 23 is governed by the control unit 20 which in turn is connected with the user interface 14 such that the user can issue directions and commands for operation of the electrosurgical generator 1. The control unit 20 generates corresponding control signals and governs the relevant components of the internal circuitry 2 according to these instructions and commands. According to this, the inverter 23 generates high-frequency alternating voltage which is to be supplied to the electrosurgical instrument 19. To achieve this, the high-frequency high-voltage output emitted by the inverter 23 is routed via an output connection 24 to the output socket 3. The output connection 24 typically comprises two conductors, one for a neutral electrode NE and one other for an active electrode AE, which comprises a DC blocking capacitor 25 in its conductor. The electrosurgical instrument 9 with its cable 93 and attached plug 94 can be plugged into the output socket 3. Actual voltage and current of the high-frequency alternating voltage as being supplied to the output socket 3 are measured by a voltage/current sensor 28. Its measurement signals are fed back by a feedback unit 29 to the control unit 20 of the electrosurgical generator 1.

The output socket 3 comprises a casing 4 having a plug socket 5 configured to receive the plug 94 of the electrosurgical instrument 9, the plug socket 5 being positioned at a frontal face of the casing 4 in order to be readily accessible. Inserted into the casing 4 is a conductor board 6 and a connector 7 attached to the conductor board 6, the connector 7 being positioned at the backside of the casing 4 (see also FIGS. 4*a* and 4*b*). Attached to this connector 7 are the high-power high-frequency alternating voltage lines, namely the power delivered via the output connection 24 to the output socket 3, and other data and/or signal lines which are symbolized by a dashed line 26 for communication and data interchange with the output socket 3 and preferably also with the instrument 9 connected via its plug 94.

There may be various electrosurgical instruments 9 of different kinds being differently configured, e.g. unipolar or bipolar, and having different plugs 94 to be attached into one of a variety of different output socket 3, 3', 3". The plugs 94 may be differently configured, in particular they may have one or two prongs 95 for the high-frequency alternating voltage, depending on whether it is a unipolar or bipolar electrosurgical instrument 9. Further, an additional prong 96 may be provided for data signals but data transmission may also be contactless.

In FIGS. 3*a* and 3*b* a front and a back view of a front plate 11 of the housing 10 are shown. The front plate 11 is configured with various examples of such different output sockets 3, 3', 3". As it can be readily appreciated in FIG. 3*a*, the output sockets 3, 3', 3" all have the same size and share the same external contour, thereby enabling them to be placed in identical cutouts. Further shown is an output socket 8 of a second group which is smaller and is configured for providing neutral earth potential. For illustrational purpose, a spare cutout 18 is depicted in FIG. 3*a*, 3*b* by a dashed line. Accordingly, any of the output sockets can be placed into one of the cutouts without requiring any further modification. This facilitates equipping the electrosurgical generator 1 with different output sockets 3, 3', 3".

The configuration of the output socket 3 with its conductor board 6 is shown in FIG. 4*a*, 4*b* and FIG. 5. The conductor board 6 is inserted exchangeable into the casing 4. Alternative embodiments of the conductor board 6', 6" that may exchangeably be inserted into the casing 4 are shown in FIG. 6*a*, 6*b*. The casing 4 features a general box-like construction and is shown in partly cutaway perspective views in FIG. 4*a*, 4*b*. At the frontal face of the casing 4 the plug socket 5 is positioned. The plug socket 5 is configured to receive the plug 94 with its prongs 95 of the electrosurgical instrument 9. Various alternative embodiments of the plug sockets 5', 5", 5 can be seen in FIGS. 1 and 3*a*. A light guide 44 is further provided at the front face and is framing the external perimeter of the plug socket 5. Accordingly, the plug socket 5 framed by the light guide 44 is illuminated, and further color-coded status signals can be conveyed to the user if the illumination is made in various colors.

The rear face of the casing 4, as shown in FIG. 4*b*, features a generally open construction. From this opening the conductor board 6 is to be inserted into the casing 4 and affixed therein. At the rear end of the conductor board 6 the connector 7 is provided configured for connecting the casing 4 with its conductor board 6 to the internal circuitry 2 of the electrosurgical generator 1. It conveys the high-frequency high voltage power as well as data and signal lines. To this end a separator 70 is provided which delimits two portions 71, 72 of the connector 7. The separator 70 may be a structural element or it may be a predefined spacing having a predefined minimum distance for proper spatial separation to high-voltage lines.

The portion 71 is configured for accepting data and signal lines and connecting these to conductors of the conductor board 6, whereas the portion 72 is configured for connecting the high-power high-frequency alternating voltage as generated by the inverter 23 and conveyed to the output socket 3 by the output connection 24. The portion 72 may connect the high-power lines, in particular the output connection 24 of the inverter 23, likewise to conductors of the conductor board 6; but in a preferred alternative as depicted in FIG. 4*b*, this portion 72 of the connector 7 is connected via direct high-voltage wiring 74, 75 to the respective contacts of the plug socket 5 accepting the prongs 95 of the plug 94 of the electrosurgical instrument 9. Thereby an efficient separation of the high-voltage lines from data/signal lines can be achieved within the casing 4 of the output socket 3. For connecting the output socket 4 to the internal circuitry 2 of the electrosurgical generator 1, no further action is required rather than putting a respective plug into the connector 7. No further connections are required, in particular it is not required to connect single wires to locations at or in the output socket 3. This allows for an efficient assembly and removes any risk of confusion or mis-attaching of wires.

The conductor board 6 with its components will be explained in more detail with reference to FIG. 5. Further, the plug socket 5 with its surrounding light guide 44 is shown. At a rear side (lower portion in the figure) of the conductor board 6 the connector 7 is shown that is mounted directly on the conductor board 6. At a front side close to a lateral edge of the conductor board 6, a light emitting device 81 is mounted. The light-emitting device 81 is located at a unitary position 82 in front of an appendage 45 of the light guide 44, the appendage 45 functioning as an entrance for light emitted by the light emitting device 81. In order to illuminate the light guide 44 in different colors, the light emitting device 81 features a plurality of LEDs having different colors, in particular red, green and yellow; however, a multi-color LED may also be used. By virtue of the unitary position 82, a proper coupling of the light as emitted by the light-emitting device 81 into the light guide 44 can be achieved regardless of the actual configuration of the conductor board 6 and/or the light-emitting device 81, thereby facilitating usage of a different conductor board.

Further, the conductor board 6 is equipped with a contactless interface 64, in particular a RFID device. It may further be equipped with a proximity sensor 65 which is configured to detect whether or not a plug 94 is plugged into the plug socket 5. Further, the contactless interface 64 may be provided with a data interface 66. Two purposes can be realized by means of the proximity sensor 65 and/or the data interface 66: firstly, it can be detected whether or not an electrosurgical instrument 9 is plugged into the output socket 3, and secondly—if the electrosurgical instrument 9 is plugged in—it can be determined which kind or type of electrosurgical instrument 9 is connected.

By means of said contactless interface 64, in particular as a RFID device, an internal memory 92 of the electrosurgical instrument 9 may be read out thereby providing additional data about the type, kind of the electrosurgical instrument 9 and/or of specifics about usage of the electrosurgical instrument 9. Further by means of said interface it may be possible to read certain modes of operation ("modes") from the internal memory 92 of the electrosurgical instrument 9 and to convey this information via the connector 7 to the control unit 20 of the electrosurgical generator 1 such that the electrosurgical generator 1 can be operated according to said mode.

Further, driving electronic components 60 can be provided on the conductor board 6, and further a control electronic component 68 can be provided for controlling the various components of the conductor board 6 including the contactless interface 64. Additionally, a supplemental data interface 69 may be provided on the conductor board 6 that is configured to communicate with certain devices on the electrosurgical instrument 9, like a hand switch 91 provided on the body of the electrosurgical instrument 9. The data interface 69 may also be configured to communicate with a data source of the electrosurgical instrument 9, for example the internal memory 92. Thereby activities of the user, like actuating the hand switch 91 can be detected and the information can be propagated via the connector 7 and the data line 26 to the control unit 20 of the electrosurgical generator.

Yet further, in order to distinguish the various output sockets 3 with their conductor boards 6 properly, a modular identifying unit 67 is provided on the conductor board 6. It is configured to identify type of the output socket 3 and functionality of its conductor board 6. This modular identifying unit 67 communicates with the internal circuitry 2 of the electrosurgical generator 1, in particular its control unit 20. By virtue of this modular identifying unit 67, the control unit 20 can determine 9 which kind of output socket 3 are installed and which are their capabilities, and based thereon the control unit 20 can (self) configure the electrosurgical generator 1 and/or adjust operation of the electrosurgical generator 1. The modular identifying unit 67 may be configured as an passive or active unit, like having a resistor or R/C network, or being active, like being equipped with a microprocessor or (E)EPROM for more granular or complex identification.

All the functionalities and the necessary connections therefore can be achieved by connecting the (single) connector 7 to the internal circuitry 2 of the electrosurgical generator 1. This is much easier than performing single wiring and by far less error prone. Alternative embodiments of the conductor board 6' and 6" are shown in FIGS. 6*a* and 6*b*. These are conductor boards having different functionality and which can be inserted into the same casing 4 to form a different output socket 3', 3", if required with a different plug socket 5', 5", without requiring any mechanical modifications, thereby maintaining the benefits and ease of mounting and connecting.

Conductor board 6' is a simplified version having fewer components. The light-emitting device 81' is equipped with a single multicolor LED. However, as opposed to the embodiment shown in FIG. 5 the connector 7 features in its portion 72 two pairs of direct cabling connection 74, 75 to the plug socket 5. Conductor board 6" is another simplified version. Its light-emitting device 81" is equipped with two single color LEDs and therefore communicates a lesser number of different color-coded information. Owing to the light-emitting device 81', 81" being located at the unitary position 82 no adaption of the light guide 44 with its appendage 45 is necessary. Therefore, in a modular-like manner either of the conductor boards 6', 6" can be placed in the same casing 4 using the same type of connector 7 for connection to the internal circuitry 2 of the electrosurgical generator. Providing a variety of output socket set 3, 3', 3" is thereby much facilitated.

Various kinds of providing proper lighting to a frontal face of the output socket 3 will be described next.

In FIG. 7 a first simple but effective variant is shown having a through hole 42 at the casing 4. Said through hole 42 runs from a rear side to a front side of the casing 4. An LED 81$^{I}$ is provided at the rear end of the through hole 42 for lighting. A filter 49 is mounted at a front side of the through hole, thereby enabling coloring of the light emitted by the LED 81$^{I}$. Thereby, only the through hole 45 needs to be manufactured for an efficient and space saving mounting of the LED 81$^{I}$, and the filter 49 may be applied if a need for coloring is to be met but might be omitted in other cases for further simplification. Any driving electronics may be placed at will, thereby further reducing spatial requirements of this variant.

FIG. 8*a*-*c* shows a second variant employing a light guide 44 which is placed in a notch 43 running along three sides of a frontal face 41 of the casing 4. Said three sides are the two lateral as well the top side of the frontal face 41, however other configurations are possible, too. The outer perimeter of the structure of the casing 4 provided with the notch 43 is affixed into a hole of the frontal plate 11 of the generator housing 10. In order to achieve not only mechanical fixation but also a sealing against unwanted HF leakage, an HF sealing 31 is provided (shown in FIG. 4*a* in a exploded view). It runs circumferentially around the perimeter of the casing 4 and will be located between the frontal plate 11 and said perimeter of the casing 4 in its mounted state.

Within the notch 43, a translucent element 47 is to be placed in addition to the light guide 44. The light guide 44 sits at a bottom of the notch 43, and the translucent 47 covers the light guide. Thereby protection of the light guide 44 as well as a smooth diffusion of the light can be achieved. Owing to the light guide 44 and the translucent element 47 both being positioned in the notch 43, the perimeter of the casing 4 is not affected and therefore no additional or more complicated sealing will be required.

The light guide 44 can be provided with an optional extension 46, as shown in FIG. 8*c*. Accordingly, the light-emitting device does not need to be placed at the casing 4 but rather can be located at a more remote place, somewhere in the housing 10 of the electrosurgical generator 1. This frees up valuable space at the casing 4 and allows for a rather free positioning of the light-emitting device within the housing.

An alternative approach for providing lighting according to a third variant is shown in FIG. 9*a*-*c*. Here, the casing 4 is provided with a surrounding frame 80 carrying at least one light-emitting device, in particular an LED 81. The frame 80 thus forms the outer perimeter of the casing 4 and will be connected to the frontal plate 11, again optionally by using a sealing 31 between said frame 80 and the frontal plate 31. The frame 80 with the LED 81 is covered by a translucent front cover 47. Thereby, the additional functionalities "sealing" and "lighting" are integrated into the frame package.

In order to achieve an indirect lighting, the LED 81 is offset towards the perimeter such as to be covered by the frontal plate 11 in the mounted state. No direct light from the LED 81 will be radiated into the eyes of the user, thereby reducing eye strain.

In a fourth variant as depicted in FIG. 10*a*, *b*, a series of cutouts 40 is provided along a top edge of the frontal face 41 of the casing 4. The cutouts 40 are arranged in line with each other. In each of the cutouts 40 a LED 81 is positioned, the LEDs 81 being arranged on a LED board 80 with a spacing matching the spacing of the cutouts 40. Light from the LEDs 81 thus can be directly radiated from the cutouts 40 to the frontal face 41 of the casing 4. The dashed ellipse symbolizes the radiation of the light. Moreover, since the LED board 80 is close to the cutouts 40 it is flush within the perimeter of the casing 4, thereby avoiding any need for additional sealing.

In a fifth variant as depicted in FIG. 11*a*, *b*, also a series of cutouts 40 is provided along a top edge of the frontal face 41, similar to the fourth variant. However, in this fifth variant a light guide 44 will be used instead of LEDs in the cutouts. The light guide 44 is placed such as to radiate light through the openings for direct illumination of the frontal face 41, similar to the fourth variant. Likewise, due to the flush mounted light guide no additional sealing will be required. However, in the fifth variant no LED is required at the casing, rather the light-emitting device can be placed anywhere in the housing 10 of the generator, wherever is a convenient location. In order to convey the light to the casing, the light guide 44 is provided with an extension 46, as already explained.

In a sixth variant as depicted in FIG. 12*a*, a planar light guide 44$^{VI}$ is provided in the casing 4 and forming the frontal face in the region of the plug 5. Further, the planar light guide 44$^{VI}$ is provided with a masking 48 having a masking hole 48' around the plug socket 5. The planar light guide 44$^{VI}$ is thus positioned approximately perpendicular to the direction of inserting the plug of the electrosurgical instrument 9 into the plug socket. This allows for an efficient pinpointed lighting of the actual plug, thereby facilitating insertion of the plug of the electrosurgical instrument 9.

Similarly, in a seventh variant as depicted in FIG. 12*b*, contacting within the plug 5 is performed by means of a contact sleeve being contacted by a rear mounted contact ring 53. However, due to the sleeve/ring-configuration a socket through hole 51 is formed leading from the frontal face 41 all the way to a rear opening of the plug. There, a LED 81 is mounted in the rear opening of the socket through hole 51, being enabled to radiate light through said through hole 51 towards the frontal face 41. This allows for a simple and pinpointed illumination of the exact location where the plug of the instrument 9 needs to be inserted, with minimum effort. This variant achieves a maximum effect with a minimum of effort.

In a preferred embodiment as shown in FIG. 13-16*b*, the conductor board 6 is configured as an angled printed circuit board assembly 6*, comprising a horizontally extending conductor board 62 and a vertically extending conductor board 61. On a rear end of the horizontally extending conductor board 62 the connector 7 is mounted. The angled printed circuit board assembly 6* with its components will be explained in more detail with reference to FIG. 13*a*, *b* and FIG. 14*a*, *b*. At a rear edge 628 of the horizontally extending conductor board 62 the connector 7 is shown. At the opposite end, namely the front edge 626 of the horizontally extending conductor board 62 the vertically arranged conductor board 61 is arranged.

A bottom view of the circuit board assembly 6* in a non-angled state is shown in FIG. 13*a*, and in FIG. 13*b* a perspective view of the assembly being transferred in its angled state is shown. On the horizontally extending conductor board 62 the conductors 625 can be seen connecting the area where the connector 7 (symbolized by dashed lines) is to be mounted with the vertically extending conductor board 61 via a flexible inter-connector 65. Conductor board 61 is provided with electric components, like a plurality of light sources 612 and/or a proximity sensor 611 of an RFID type which is configured to detect whether or not a plug 94 is plugged into the plug socket 5.

Similarly, the horizontally extending conductor board 62 can be provided with electric components, like a contactless interface 622 which is configured to determine which kind or type of electrosurgical instrument 9 is plugged in and forwards corresponding data by the data lines of the connector 7 and the data line 26 to the control unit 20 of the electrosurgical generator 1.

Further, the conductor board 61 is provided with two clearance holes 60, 60' which are being shaped and dimensioned such as to allow for passage of a body 56 of each of the plug socket 5, 5'. The light sources 612 are arranged along the perimeter of the clearance holes 60, 60'.

In the embodiment as shown in FIG. 14*a*), the horizontally extending conductor board 62 is attached to a lower edge 617 of the vertically extending conductor board 61; attaching to an upper edge 616 would also be possible. This provides for a flat orientation and a rather large surface of the horizontally extending conductor board 62, thereby facilitating positioning of even complex electrical circuits with many components. Alternatively, as shown in FIG. 14*b*) the horizontally extending conductor board 62' may also be attached to a lateral side of the vertically extending conductor board 61, in the depicted embodiment to the left lateral side 618. Thereby an alternative angled printed circuit assembly 6 can be formed. Obviously, it is also possible to position the horizontally extending conductor board 62' at the other, the right lateral side 619. This configuration has the advantage of providing a rather large clear space behind the vertically extending conductor board 61** without any obstructions, thereby facilitating air streaming in a vertical direction for improved cooling.

A preferred embodiment of the angled printed circuit board assembly 6* being a rigid-flex printed circuit board having the flexible inter-connector formed as a unitary piece is shown in detail in FIG. 15*a, b*. These figures show the flexible inter-connector 65 in an original flat state in FIG. 15*a* and in an operative angled state are shown in FIG. 15*b*. The flexible inter-connector 65 is a unitary piece that features extensions arranged on one of the main surfaces of either conductor board 61, 62. For achieving the operative position, namely the angled state of the conductor board assembly 6*, the conductor board 61 is moved into a vertical position which requires no further action than just tilting this board 61 into the appropriate position as the flexible interconnector 65 will follow as needed. The advantage is that no specific connection is to be made and that the two conductor boards 61, 62 are thereby inseparably joined together. Positional variations, in particular with respect to the angular position, will be well tolerated by the flexible inter-connector 65, thereby providing an easy to assemble and robust connection of the horizontally extending conductor board 61 in the vertically extending conductor board 62 of the angled printed circuit board assembly 6*.

A perspective view and a cross-section of the casing 4 with the angled printed circuit conductor board assembly 6* in its assembled position are shown in FIGS. 16*a* and *b*. Two socket plugs 5, 5' are shown which are positioned in the clearance holes 60, 60' having their body 56 placed in the large space behind the front face 41 of the casing 4. At the rear of the body 56 of either socket plugs 5, 5' having contact tabs 55 are shown which are configured to receive the direct wiring 74, 75 (as shown in FIG. 4*b*) for supply of the high-frequency high voltage from the connector 7.

Correct positioning of the plug socket 5 at the front face 41 is ensured by a clamping device 54 which is configured as a nut. It is to be tightened such as to force the plug socket 5 into a defined position with respect to the front face 41. In the depicted embodiment, also the vertically extending conductor board 61 is placed under the nut of the clamping device 54, thereby also affixing the conductor board 61 to the frontal face 41 and thereby increasing stability.

Further, an appendage 45 having an entry portion of the light guide 44 is shown. Due to the angled position of the vertically extending conductor board 61, the light source 612 mounted thereon is automatically positioned in front of said entry portion of the appendage 45 upon inserting and assembling of the angled printed circuit board assembly 6* into the casing 4. This allows for efficient manufacturing and assembly of the output socket 3.

The other output sockets 3', 3" are likewise configured and assembled; they mainly differ in number and kind of the plug sockets 5, 5'.

Final assembly can be achieved just by placing the output socket 3, 3' with its casing 4 into its position at the front face 11 of the housing 10 of the electrosurgical generator 1 and to connect the connector 7 to the internal circuitry 2 of the electrosurgical generator 1.

The invention claimed is:

1. An electrosurgical generator comprising a housing, and internal circuitry configured to generate a high-frequency voltage and output the generated high-frequency voltage to an electrosurgical instrument, the electrosurgical generator further comprising at least one output socket for connection of a plug of the electrosurgical instrument, said at least one output socket forming part of the housing and being configured as a self-contained unit comprising:

a casing configured for mounting at a front plate of the housing; and a plug socket mounted at a frontal face of the casing for plugging of in the electrosurgical instrument;

wherein the at least one output socket is further provided with a conductor board that is inserted into the casing and configured to provide internal connections of the output socket, and a connector provided at the conductor board that is configured to connect to the internal circuitry of the electrosurgical generator, wherein the conductor board is provided with a control electronic component which is configured to control other components on the conductor board.

2. The electrosurgical generator as claimed in claim 1, wherein the at least one output socket is selected from a group of output sockets being configured differently, wherein the casings of the output sockets of said group have an identically sized and contoured external perimeter; and/or wherein the conductor board is selected from a plurality of conductor boards having different functionality, said conductor boards being mechanically exchangeable in the casing.

3. The electrosurgical generator as claimed in claim 1, wherein the control electronic component is communicatively connected to a control unit of the internal circuitry, wherein the control electronic component is configured to perform instrument related data processing as a sub-station to the control unit, and/or to control the electrosurgical instrument via a prescribed process, said prescribed process comprising a sequence of activation steps for the electrosurgical instrument.

4. The electrosurgical generator as claimed in claim 3, wherein the conductor board is further provided with a signaling device, and/or a light-emitting device, interacting with the control electronic component for signaling status information to a user, said status information being status information of at least one of the internal circuitry, the electrosurgical instrument or the prescribed process.

5. The electrosurgical generator as claimed in claim 1, wherein the conductor board is provided with a module identifying unit configured to communicate with the internal circuitry, the module identifying unit being further configured to identify type and/or functionality of the output socket; and/or wherein a supplementary data interface is provided on the conductor board and is configured to communicate with signaling devices on electrosurgical instruments; and/or wherein further the conductor board is provided with driving electronic components for light-emitting devices and/or contactless interface, said contactless interface being configured to communicate with the electrosurgical instrument.

6. The electrosurgical generator as claimed in claim 1, wherein the control electronic component is configured to interact with at least one of a module identifying unit, supplementary data interface, driving components for light emitting devices, or a contactless interface.

7. The electrosurgical generator as claimed in claim 1, wherein the casing is provided with a light guide configured for illuminating a front portion of the casing, wherein the light guide is provided with an extension being configured for a remote light feed.

8. The electrosurgical generator as claimed in claim 1,
wherein the casing is provided with a receptacle for a light-emitting device, and/or the conductor board is provided with a light-emitting device;
wherein the light-emitting device is configured for supplying light into a light guide, and/or into a translucent insert which is colored.

9. The electrosurgical generator as claimed in claim 1,
wherein the casing is provided with a surrounding frame holding at least one light-emitting device, said frame being configured for attachment to a frontal plate of the casing,
wherein a translucent front cover is provided for the frame with its at least one light-emitting device, said translucent front cover and/or the frame being provided with a sealing configured to interact with the frontal plate, said translucent front cover being configured for indirect lighting by having the at least one light-emitting device offset such as to be at least partly covered by the frontal plate.

10. The electrosurgical generator as claimed in claim 8, wherein the light-emitting device is placed at a unitary position on the conductor board, at an entry of the light guide, and/or said light-emitting device is configured for emitting light having different colors.

11. The electrosurgical generator as claimed in claim 1, wherein at least one cutout is provided at an edge of the casing, the at least one cutout having an opening to a frontal face of the casing and being configured as a receptacle for a light guide or a light emitting device.

12. The electrosurgical generator as claimed in claim 11,
wherein a seating for an illumination board is provided at the at least one cutout, the illumination board carrying at least one light-emitting device, and/or
wherein a light guide is positioned within the at least one cutout or a series of cutouts such as to emit light therethrough to the frontal face, said cutouts of the series in line with each other and enabling a single light guide to be threaded through them.

13. The electrosurgical generator as claimed in claim 1,
wherein the frontal face of the casing at least in a region of the plug socket is formed by a planar light guide being provided with a masking having a masking hole around the plug socket;
wherein the planar light guide is oriented perpendicular to a plugging direction of the plug socket, and light is provided by a light-emitting device positioned at an edge of the planar light guide and/or by a second light guide connecting to said planar light guide.

14. The electrosurgical generator as claimed in claim 1,
wherein the plug socket comprises a hollow interior and an opening is provided at a rear end of the plug socket, wherein a light-emitting device is positioned at said opening and being configured to emit light through the hollow interior to the frontal face of the casing,
wherein the plug socket is provided with a sleeve as internal contact for the plug of the electrosurgical instrument, and optionally a translucent element is positioned within said sleeve.

15. The electrosurgical generator as claimed in claim 1, wherein the casing is provided with a circumferential HF sealing configured such as to bear on a frontal plate of the casing in its mounted state.

16. The electrosurgical generator as claimed in claim 1, wherein a second group of casings is provided having a different external perimeter for output sockets configured for a different kind of electrosurgical instrument.

17. The electrosurgical generator as claimed in claim 1,
wherein the connector is mounted directly on the conductor board, and/or
the at least one output socket comprises an integrated high-frequency conductor line, said high-frequency conductor line being comprised in the connector with a separator or in a dedicated sub-connector for protection of signal lines, and terminating at the plug socket.

18. The electrosurgical generator as claimed in claim 1,
wherein said conductor board is configured as an angled printed circuit board assembly comprising
a vertically extending conductor board located adjacent to a front of the casing, a horizontally extending conductor board located rearward of the vertically extending conductor board and being oriented such as to point rearward, and an inter-connector providing electrical connections between said conductor boards, wherein the horizontally extending conductor board is provided
with the connector for connection to the internal circuitry and
with conductors for conveying electrical energy to the vertically extending conductor board,
wherein the vertically extending conductor board is provided with at least one light source configured to emit light for illuminating the plug socket.

19. The electrosurgical generator as claimed in claim 18,
wherein the inter-connector between the conductor boards is a flexible inter-connector, wherein the flexible inter-connector is attached in a fixed manner at one or both of said conductor boards,
wherein the horizontally extending conductor board, the flexible inter-connector and the vertically extending conductor board are formed as a unitary piece.

20. The electrosurgical generator as claimed in claim 18,
wherein conductors of the conductor boards are configured as impedance-controlled conductors, conductors of the inter-connector are also configured as being impedance-controlled; and/or wherein a high-frequency line supplying the high-frequency voltage to the output socket comprises a direct connection from the connector to the plug socket, said direct connection bypassing the inter-connector between the conductor boards.

21. The electrosurgical generator as claimed in claim 18, wherein the vertically extending board is provided with a clearance hole for the plug socket, the clearance hole being configured for allowing passage of a body of the plug socket.

22. The electrosurgical generator as claimed in claim 1, wherein the conductor board is further provided with a light-emitting device interacting with said control electronic component on said conductor board, said light-emitting device being configured to signal status information to a user.

23. The electrosurgical generator as claimed in claim 1, wherein the at least one output socket is placed with its casing into a cut-out of the housing.

* * * * *